(12) United States Patent
Philippon et al.

(10) Patent No.: US 10,709,563 B2
(45) Date of Patent: Jul. 14, 2020

(54) FEMORAL NECK SUPPORT STRUCTURE, SYSTEM, AND METHOD OF USE

(71) Applicants: MJP INNOVATIONS, INC., Edwards, CO (US); Marc Prisant, Edwards, CO (US)

(72) Inventors: Marc J. Philippon, Vail, CO (US); David L. Bombard, Edwards, CO (US); John Michael Egan, Hollywood, FL (US)

(73) Assignee: MJP Innovations, Inc., Edwards, CO (US)

( * ) Notice: Subject to any disclaimer, the term of this patent is extended or adjusted under 35 U.S.C. 154(b) by 135 days.

(21) Appl. No.: 15/943,157

(22) Filed: Apr. 2, 2018

(65) Prior Publication Data

US 2018/0325680 A1 Nov. 15, 2018

Related U.S. Application Data

(60) Division of application No. 14/948,537, filed on Nov. 23, 2015, now Pat. No. 9,931,214, which is a
(Continued)

(51) Int. Cl.
*A61F 2/32* (2006.01)
*A61F 2/36* (2006.01)
(Continued)

(52) U.S. Cl.
CPC ............ *A61F 2/3609* (2013.01); *A61B 17/68* (2013.01); *A61B 17/74* (2013.01); *A61B 17/742* (2013.01); *A61B 17/8872* (2013.01); *A61F 2/3672* (2013.01); *A61F 2/90* (2013.01); *A61B 17/7097* (2013.01); *A61B 17/8855* (2013.01); *A61F 2002/30593* (2013.01)

(58) Field of Classification Search
CPC combination set(s) only.
See application file for complete search history.

(56) References Cited

U.S. PATENT DOCUMENTS

| 4,735,625 A | 4/1988 | Davidson |
| 6,248,110 B1 * | 6/2001 | Reiley ............... A61B 17/8811 606/93 |

(Continued)

FOREIGN PATENT DOCUMENTS

| WO | WO 01/28443 A1 | 4/2001 |
| WO | WO 01/54598 A1 | 8/2001 |

OTHER PUBLICATIONS

Arillo, Fernandez J., "Extended European Search Report re Application No. 08 84 5834.4-1654", Jan. 21, 2014; p. 12, EPO.
(Continued)

*Primary Examiner* — Sameh R Boles
(74) *Attorney, Agent, or Firm* — Da Vinci Partners LLC; John Moetteli

(57) ABSTRACT

A device for reinforcing a femoral neck bone, the femoral neck bone including a cortical bone region and a cancellous bone region, the device including a support structure having an outer surface and including a portion having one or more bores, the one or more bores adapted to allow filler material to be released therefrom to enter directly into the cancellous bone.

8 Claims, 20 Drawing Sheets

Related U.S. Application Data continuation of application No. 14/624,304, filed on Feb. 17, 2015, now Pat. No. 9,220,545, which is a continuation of application No. 13/784,948, filed on Mar. 5, 2013, now Pat. No. 8,986,308, which is a division of application No. 12/259,929, filed on Oct. 28, 2008, now abandoned.

(60) Provisional application No. 60/983,882, filed on Oct. 30, 2007.

(51) Int. Cl.
*A61B 17/68* (2006.01)
*A61B 17/74* (2006.01)
*A61B 17/88* (2006.01)
*A61F 2/90* (2013.01)
*A61B 17/70* (2006.01)
*A61F 2/30* (2006.01)

(56) References Cited

U.S. PATENT DOCUMENTS

| | | |
|---|---|---|
| 6,261,289 B1 | 7/2001 | Levy |
| 7,241,303 B2 | 7/2007 | Reiss et al. |
| 7,261,720 B2 | 8/2007 | Stevens et al. |
| 2002/0032444 A1 | 3/2002 | Mische |
| 2002/0055742 A1 | 5/2002 | Lieberman |
| 2003/0050644 A1 | 3/2003 | Boucher et al. |
| 2005/0169893 A1 | 8/2005 | Koblish et al. |
| 2006/0264950 A1 | 11/2006 | Nelson et al. |
| 2006/0271196 A1 | 11/2006 | Saal et al. |
| 2007/0093899 A1 | 4/2007 | Dutoit et al. |

OTHER PUBLICATIONS

International patent application No. PCT/US08/81541, International Search Report, dated Jan. 29, 2009.
Liberman, Uri A. et al., Effect of Oral Alendronate on Bone Mineral Density and the Incidence of Fractures in Postmenopausal Osteoporosis, New Eng. J. Med., Nov. 30, 1995.

* cited by examiner

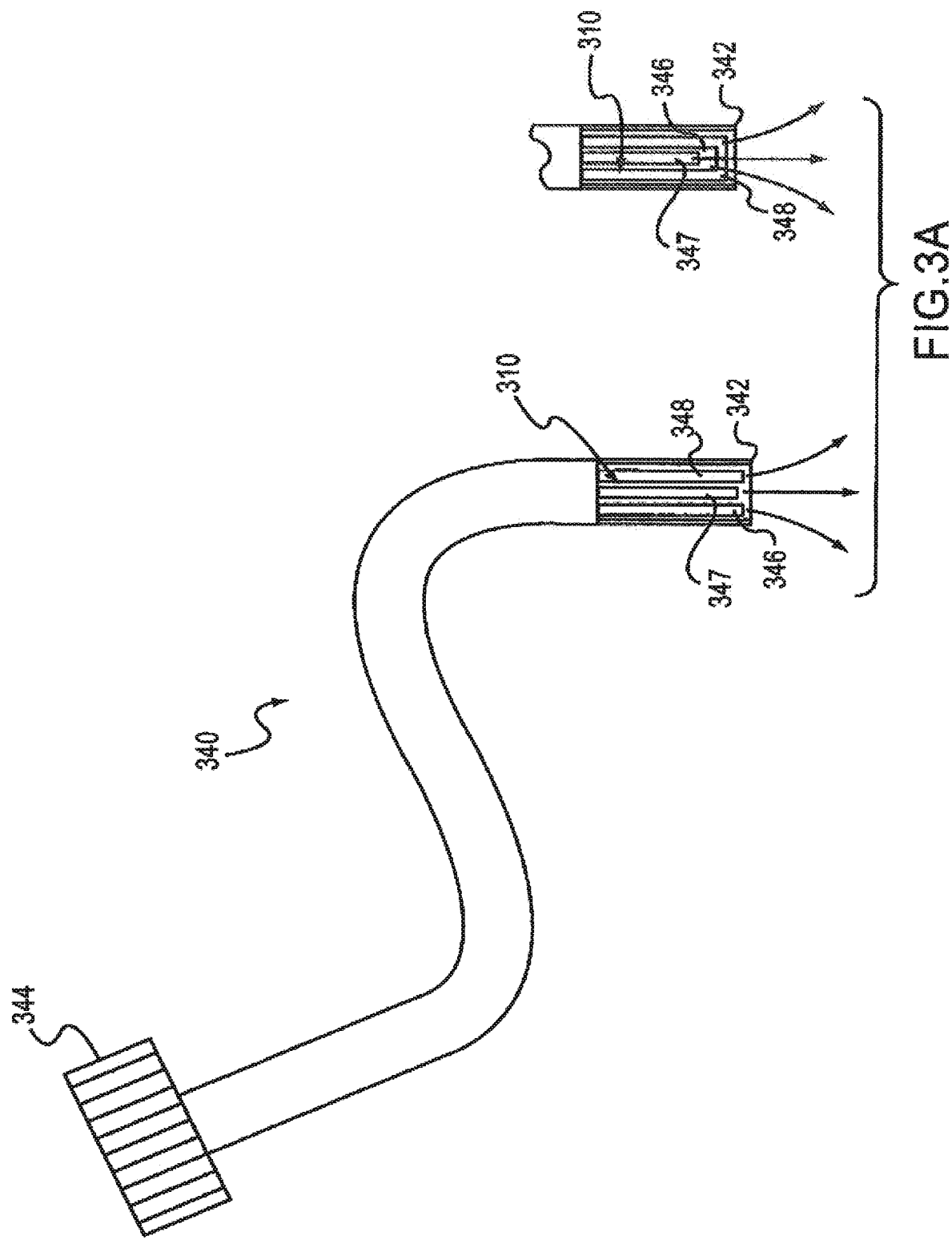

FEMORAL NECK SUPPORT STRUCTURE, SYSTEM, AND METHOD OF USE

PRIORITY AND CROSS REFERENCE TO RELATED APPLICATIONS

The present application is a divisional application of a continuation of U.S. patent application Ser. No. 13/784,948 filed Mar. 5, 2013, which is divisional of, and claims the benefit of U.S. patent application Ser. No. 12/259,929 filed Oct. 28, 2008, which itself claims the benefit of Provisional U.S. Patent Application No. 60/983,882 filed Oct. 30, 2007. The details of application Ser. Nos. 13/1784,948, 12/259,929 and 60/983,882 are incorporated by reference into the present application in their entirety and for all proper purposes.

FIELD OF THE INVENTION

Aspects of the present invention relate generally to medical devices. In particular, but not by way of limitation, aspects of the present invention relate to femoral neck support devices, systems, and methods for operating the same.

BACKGROUND OF THE INVENTION

Bone fractures within the hip joint can cause debilitating and life-threatening conditions. Statistics show that 50% of people over 50 years of age who suffer a fracture in a hip joint bone die within the first year. One area of the hip that often fractures is the femoral neck. The femoral neck is the portion of the femur which integrates the body of the femur extending from the knee joint, to the femoral head, which fits within the socket of the hip joint (Acetabulum).

The femoral neck is especially prone to fractures in persons suffering from osteoporosis, where bone density is reduced. Further conditions, such as, but not limited to, diseased trabeculae in the Ward's triangle region of the femoral neck may also increase the risk of femoral neck fractures. Common approaches to reducing femoral neck fractures include augmenting the strength of the femoral neck by increasing bone density.

One way bone density is increased in the femoral neck is through the use of pharmaceuticals. However, relatively minimal increases in femoral neck bone density have been attributed to pharmaceutical treatments. For example, one study shows an increase in femoral neck bone mass density of only about six percent due to pharmaceutical use. See Uri A. Liberman, M.D., Ph.D., et al., Effect of Oral Alendronate on Bone Mineral Density and the Incidence of Fractures in Postmenopausal Osteoporosis, The New England Journal of Medicine, Nov. 30, 1995. This increase is at the upper end of bone mass density increases, as other studies show significantly less increase in femoral neck bone mass density due to pharmaceutical use. Additionally, the use of pharmaceuticals can have serious side effects such as chest pain, difficult or painful swallowing, hot flashes, joint pain, blood clots, and ulcers in the stomach or esophagus.

General suppression of hip fractures through the use of medical devices has also been mentioned in the prior art. For example, U.S. Pat. No. 7,261,720 ('720) describes a balloon embodiment adapted to support the upper femoral area. However, the balloon embodiment described in the '720 patent does not provide adequate support and reinforcement for the femoral neck.

What is needed therefore is system and method for installing a femoral neck bone reinforcement which effectively anchors in the cancellous bone so as to allow at least a portion of the load from the femoral neck bone to be transferred to the support structure.

SUMMARY OF THE INVENTION

A device for reinforcing a femoral neck bone that solves the problems of the prior art is provided. The femoral neck bone includes a cortical bone region and a cancellous bone region. The device includes a support structure having an outer surface and including a portion comprising one or more bores. The bores are adapted to allow filler material to be released therefrom to enter directly into the cancellous bone.

In accordance with one embodiment a device for reinforcing a femoral neck bone, the femoral neck bone including a cortical bone region and a cancellous bone region, comprises a support structure deployable from a first substantially collapsed position to a second substantially expanded position, the support structure adapted to displace at least a portion of the cancellous bone region and wherein when deployed in the second substantially expanded position, the support structure structurally interacts with at least a portion of the cortical bone region.

In accordance with another embodiment, a method of reinforcing a femoral neck comprises creating a bore proximate to at least one of a Ward's triangle and a greater trochanter, creating at least one cavity in a cancellous bone region of the femoral neck, inserting a substantially collapsed support structure through the bore and into the at least one cavity, expanding the support structure, and allowing at least a portion of the load from the femoral neck bone to be transferred to the support structure.

These and other embodiments are described in further detail herein.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawings, wherein:

FIG. 3A is a side view of an actuation device having a cut-away portion near the actuator head, and a close-up side view of an actuator head cut-away portion;

DETAILED DESCRIPTION

Figure 1A:
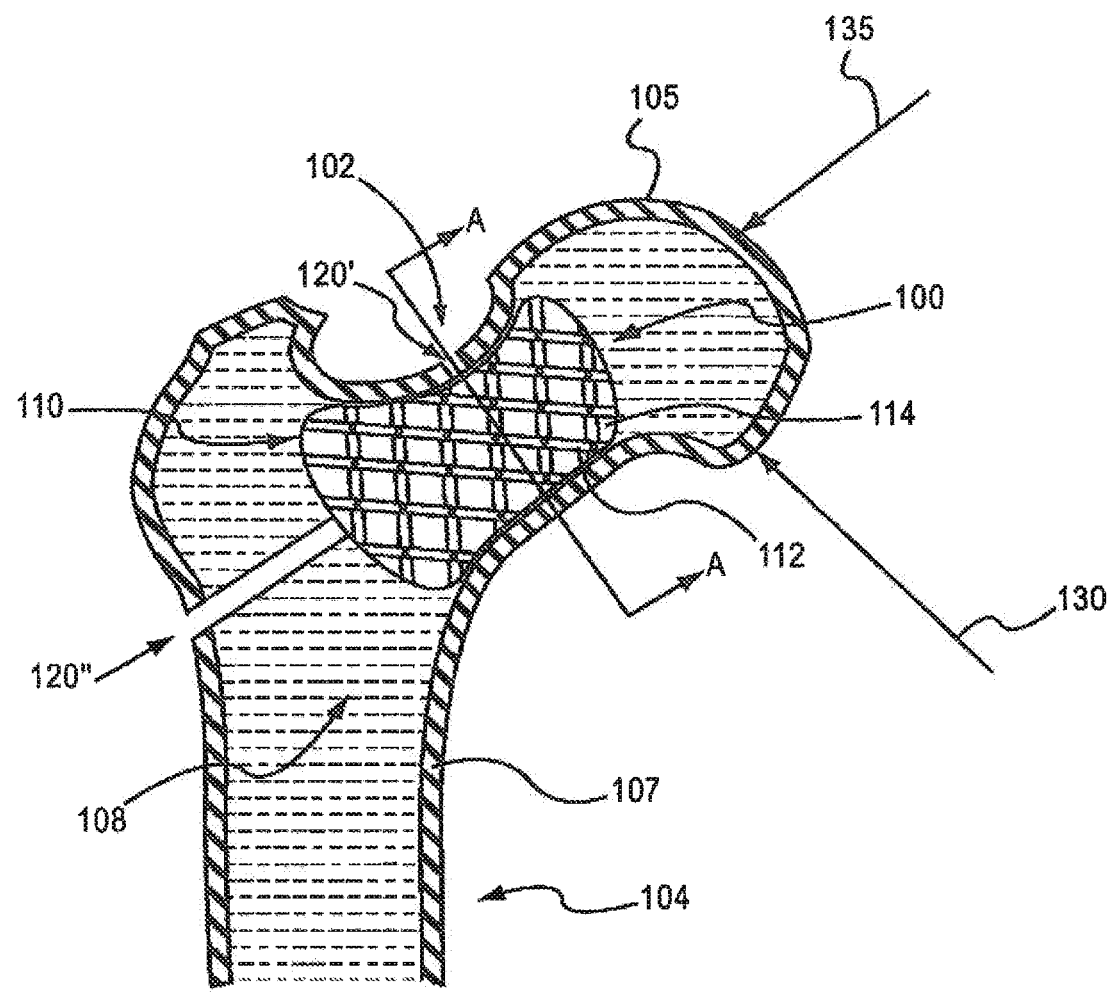
FIG. 1A is a side-view of an expanded femoral neck support structure within a femoral neck.

Referring now to the drawings, where like or similar elements are designated with identical reference numerals throughout the several views where appropriate, and referring in particular to FIGS. 1A-2B, a device 100 for reinforcing a femoral neck 102 bone is shown and described. As shown in FIG. 2A, the femoral neck 202 is a portion of the femur 204 which resides between the greater trochanter 206 and the femoral head 205, connecting the femoral body 203 to the femoral head 205, which rests in the hip joint. The device 100 is adapted to be placed inside the femoral neck 202 bone, thereby reinforcing the femoral neck 202 from the inside.

Figure 1B:
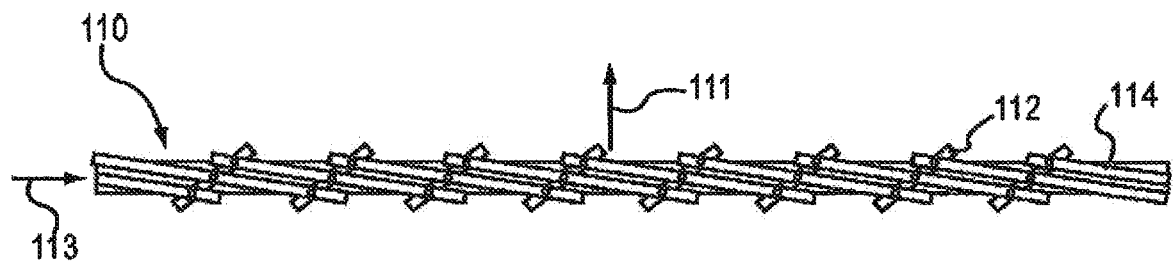
FIG. 1B is a side-view of one embodiment of a collapsed femoral neck support structure.

In one embodiment, the device 100 is comprised of a support structure 110, as shown in FIG. 1A. One support structure 110 may be deployable from a first substantially collapsed position, as shown in FIG. 1B, to a second substantially expanded position, as shown in FIG. 1A. In one embodiment, the collapsed position is used so the structure 110 may be inserted into the femoral neck 102. For example, the collapsed support structure 110 may enter the femoral neck 102 through at least one of a Ward's triangle bore 120' and a greater trochanter bore 120" and subsequently expand into the femoral neck 102.

In order to expand, one embodiment may be comprised of a stent 112 and a balloon 114. The expansion of the structure 110 into the femoral neck 102 may be actuated by expanding the balloon 114 from a location proximate a bore 120', 120" into an internal femoral neck 102 region. Other expansion techniques known in the art not using balloons are also contemplated. For example, the stent 112 may be actuated to expand from the collapsed position to the expanded position by applying at least one of a lateral force 111 and a longitudinal force 113 onto the structure 110, as shown in FIG. 1B. Such forces 111, 113 may be used on devices which are not comprised of a balloon 114. However, similar forces may also be used on devices having one or more balloons 114. Furthermore, some embodiments may be comprised of one or more stents 112 or balloons 114. Embodiments are further contemplated comprising one or more devices 100.

As shown in FIG. 1A, a femur 104 may be comprised of cortical bone 107 and cancellous bone 108. In an osteoporotic patient, or in patients having other ailments, the cancellous bone 108 may have a low bone mass density or may otherwise be relatively malleable bone matter as compared to portions of the cortical bone 107 which may be healthier, more rigid bone matter. One structure 110 is adapted to expand within the cancellous bone 108. In one embodiment, upon expansion of the support structure 110 into the femoral neck 202, a cavity 209 is created, as shown in FIG. 2B. In one embodiment, the cavity 209 is created through the expansion of the structure 210 itself. However, in other embodiments, the cavity 209 may be created prior to expansion of the structure 210. For example, a cavity may be drilled, tapped, or punched within the cancellous bone 208 and a collapsed structure 210 may be placed into the cavity 209 and subsequently expanded. In one embodiment, such as an embodiment where the structure 210 creates the cavity 209, the cancellous bone 208 may be compressed. Cancellous 208 bone may also be removed from the femoral neck 202 through a drill or otherwise. As shown in FIG. 2B, the cancellous bone 208 may be compressed between the support structure 210 and the cortical bone 207. In one embodiment, the balloon 214 may expand and compress the cancellous bone 208 and the stem 212 may subsequently be inserted into the cavity 209 created by the balloon 214 and expanded.

When deployed in the second substantially expanded position, as shown in FIGS. 1A and 2B, support structure 210 may be further adapted to interact with the cortical bone 207. In one embodiment, for example, one or more staples 215, or other similar mechanisms, may be used to couple the structure 210 to the cortical bone 207 or the compressed cancellous bone 208. However, the structure 210 may interact with the cortical bone 207 in one or more other manners as well. For example, as shown in FIGS. 1A & 2B, one embodiment may be configured to have an outer surface shape which generally forms to an inner surface of the cortical bone 107, allowing the support structure to fit snugly within the healthy cortical bone 207. Adapting the shape of the structure 110 to resemble the shape of the cortical bone 107 within the femoral neck 202 enables interaction between the structure 110 and the cortical bone 107. Interaction occurs when an external load such as, but not limited to, a peak gait load 135 or a lateral fall load 130, is applied to the femoral neck 102. In such a case, the load is transferred from the cortical bone 107 to the structure 110, allowing the structure 110 to reinforce the femoral neck 202. In at least one embodiment, load may be transferred to the structure 110 through contact between the cortical bone 107 and the structure, while in other embodiments, interaction between the cortical bone 107 and structure 110 may occur through the compressed cancellous bone 108 or bone cement.

Figure 25A:
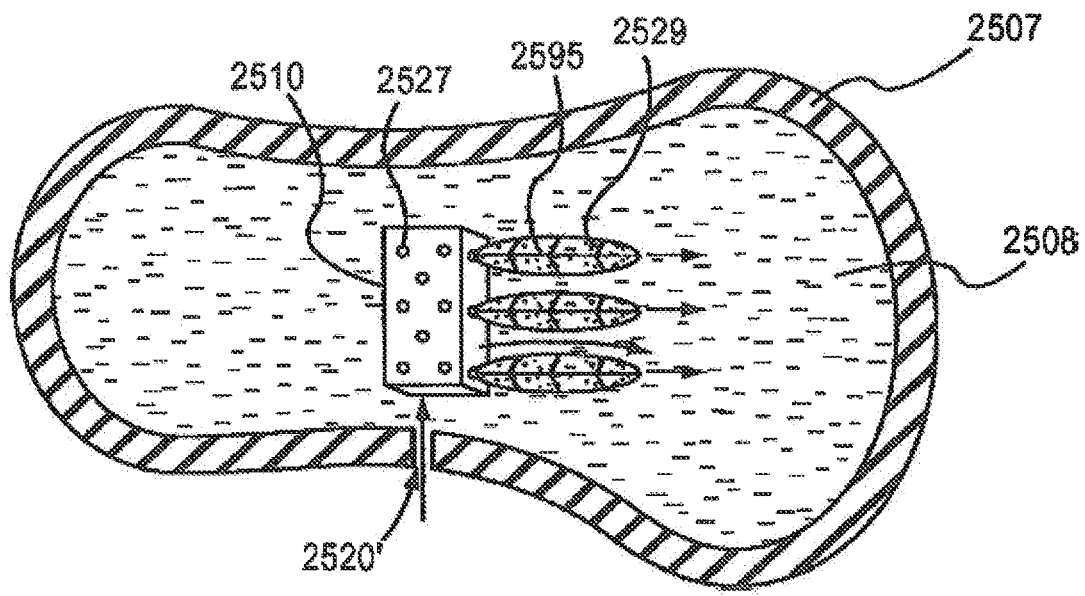
FIG. 25A is a top view of a femoral neck with an anterior Ward's triangle bore and having a femoral neck support structure located therein.
Figure 25B:
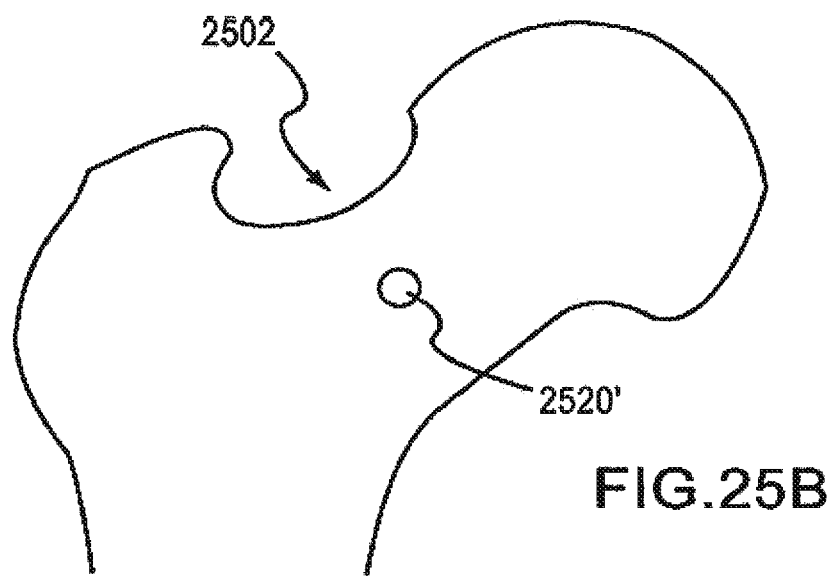
FIG. 25B is a side view of a femoral neck with an anterior Ward's triangle bore.

It should be noted that the Ward's triangle bore 120' shown in FIG. 1A and elsewhere, may comprise an anterior Ward's triangle bore 2520', located in the femoral neck 2502, as shown in FIGS. 25A and 25B. All embodiments discussed herein may enter through the anterior Ward's triangle bore 2520'. One such embodiment may comprise a support structure 2510 having a portion comprising one or more bores 2527. Through at least one of the bores 2527, a support structure section 2729 may be released into the cancellous bone 2508. Upon being released from the bore 2527, the support structure section 2729 may expand. Furthermore, filler material 2595 may be released from the bore 2527 into the cancellous bone 2508. Filler material 2595 in one embodiment may enter directly into the cancellous bone 2508 or the filler material 2595 may enter into the cancellous bone 2508 along with a support structure section 2529, as shown in FIG. 25A.

Figure 3B:
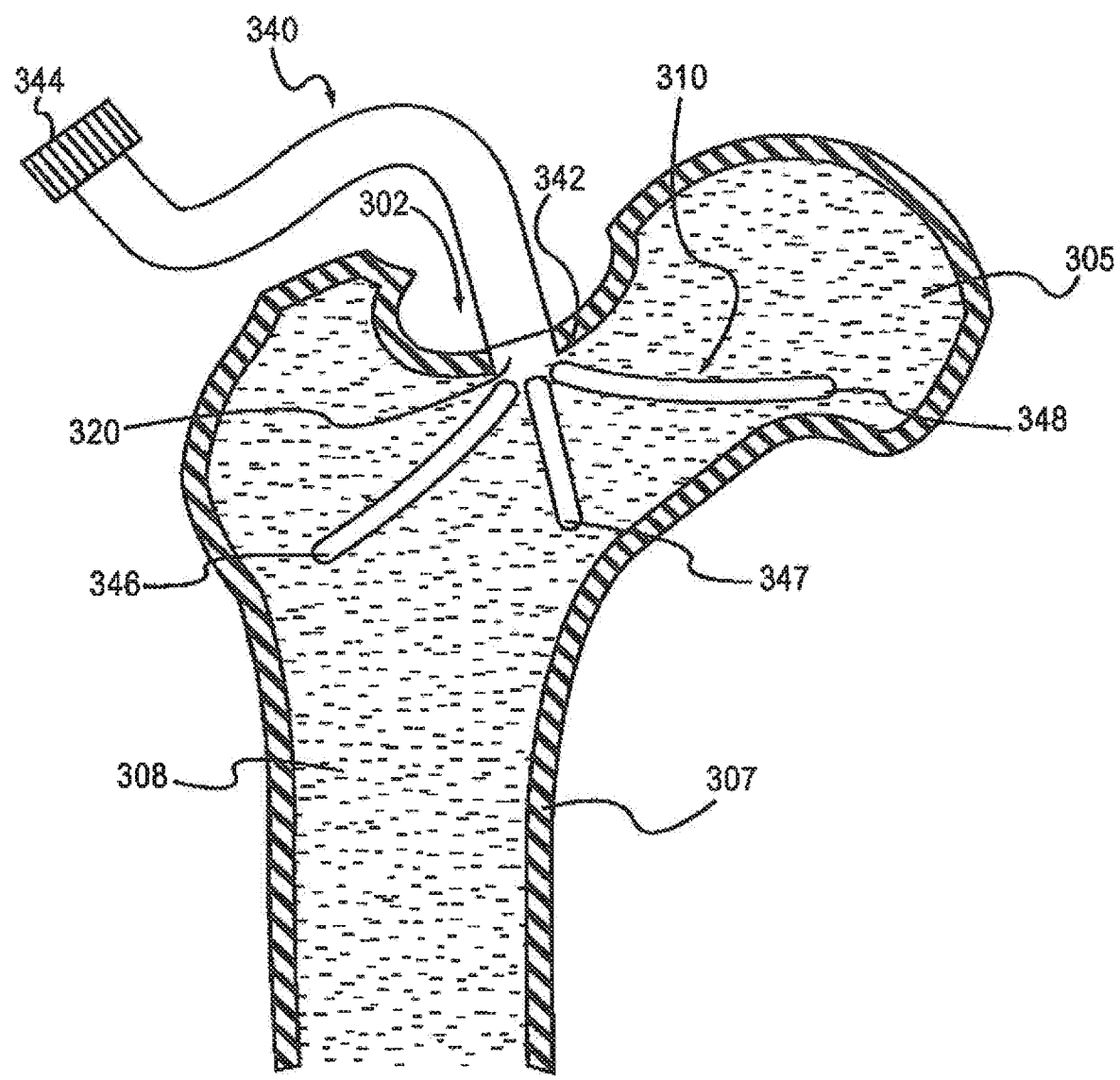
FIG. 3B is a side view of an actuation device and a support structure within a cross-section of a femoral head and neck.
Figure 3C:
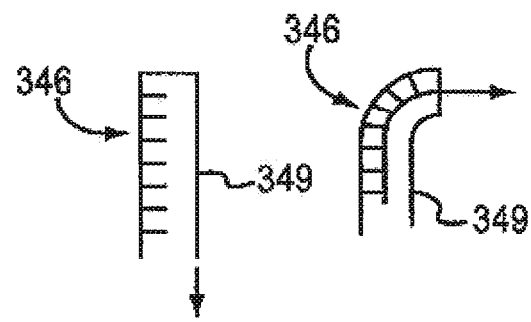
FIG. 3C is a side view of a support structure section showing how a trigger mechanism motion may be applied.

Referring to FIGS. 3A-3C, one embodiment of a femoral neck 302 support structure 310 may also include an actuation device 340. Actuation device 340 is adapted to deliver the support structure 310 to the femoral neck 302. For example, actuation device 340 may be comprised of a tube adapted to substantially enclose a compressed support structure 310. The actuation device 340 may be steerable, enabling an actuation device head 342 to be positioned proximate the femoral neck bore 320. In some embodiments, the actuation device head 342 may also be adapted to be positioned in the bore 320, the cortical bone 307, or the cancellous bone 308.

Once the actuation device head 342 is in the correct position, the support structure 310 may be deployed. Actuation device 340 may deploy the support structure 310 through a trigger mechanism 344. The trigger mechanism 344 may be adapted to steerably release separate support structure sections into separate areas of the femoral neck 302. For example, as shown in FIGS. 3A & 3B, support structure 310 may be comprised of a first section 346, a second section 347, and a third section 348. Upon actuating the trigger mechanism 344, the first, second, and third sections 346, 347, 348 are released from the tube into separate cancellous bone 308 areas. The trigger mechanism may be adapted to receive one or more pushing, pulling, or twisting motions, in order to actuate the release of the support structure 310.

A first section 346 may be designed to be released from the actuation device 340 and bend towards the greater trochanter 306 and a third section 348 may be designed to bend towards the femoral head 305. Structure sections 346, 348 may be adapted to bend in a specific direction by coupling an elastomeric band having a first length to one side of the section and coupling an elastomeric band having a longer second length to the opposing side of the section, thereby causing the section to bend towards the side having the shorter elastomeric band. Bending individual support structure sections 346, 347, 348 to a proper internal femoral neck 302 location may also occur through a motion applied at the trigger mechanism 344. For example, as shown in FIG. 3C, a pulling motion applied at the trigger mechanism 344 may be transferred to a side 349 of the first structure section 346, allowing the section 346 to bend towards the pulled side 349.

Figure 4:
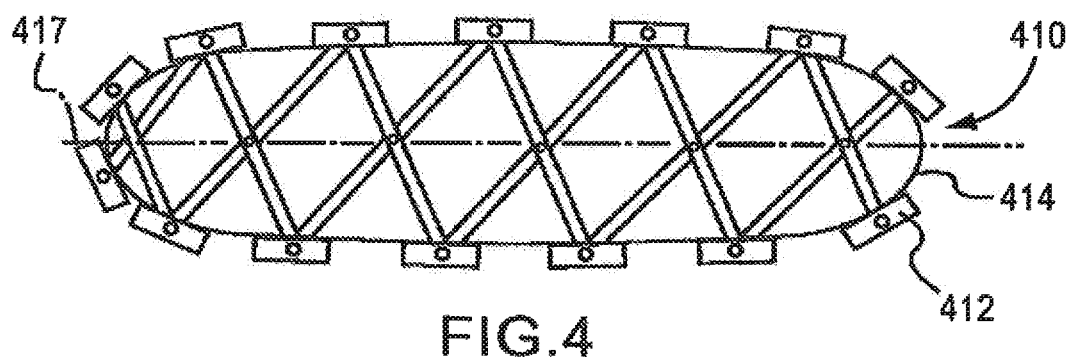
FIGS. 4-15 are various embodiments of a femoral neck support structure constructed in accordance with aspects of the present invention.
Figure 5:
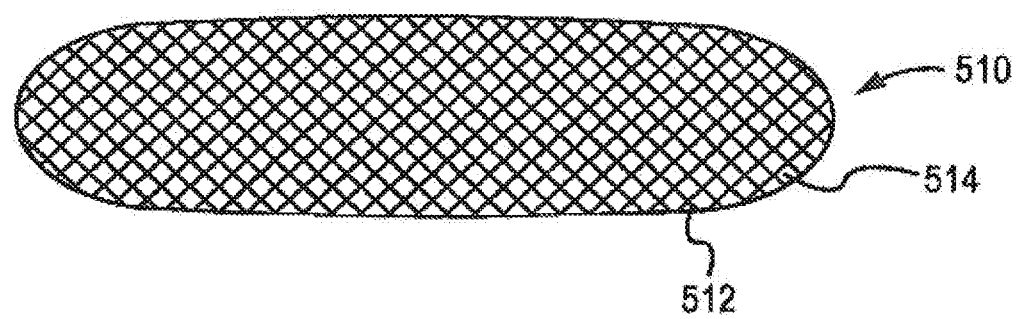
Figure 9:
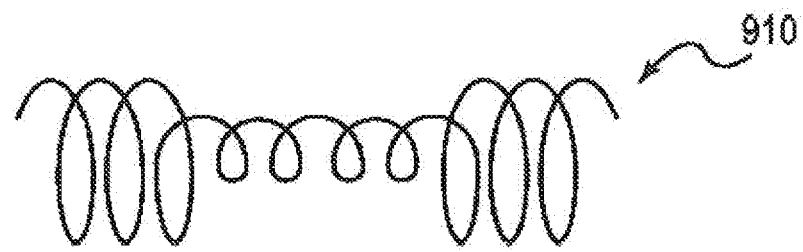
Figure 10:
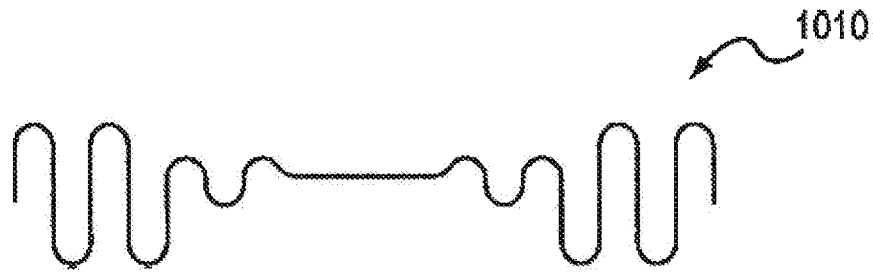
Figure 11:
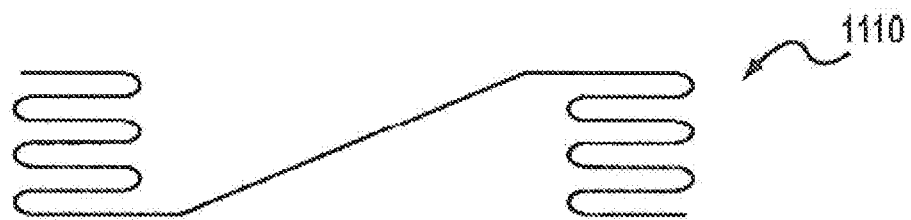
Figure 12:
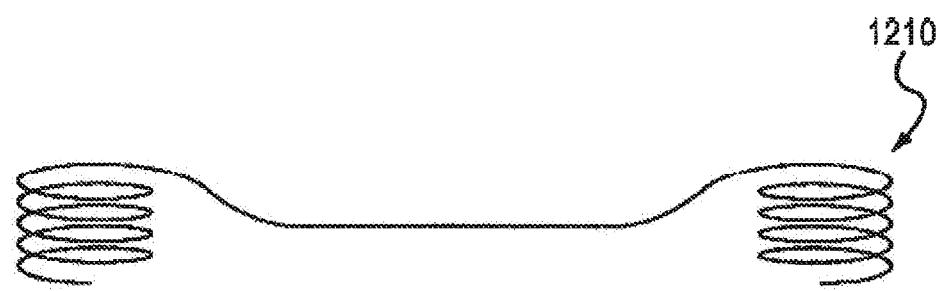
Figure 13:
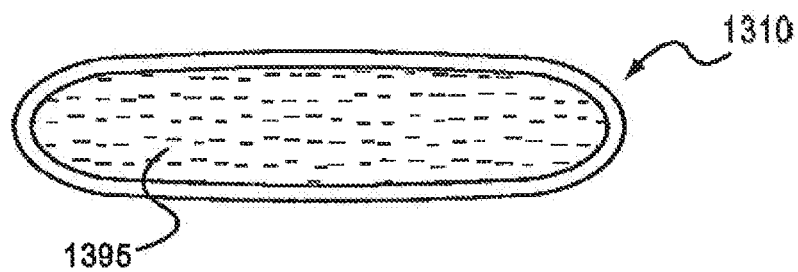
Figure 14:
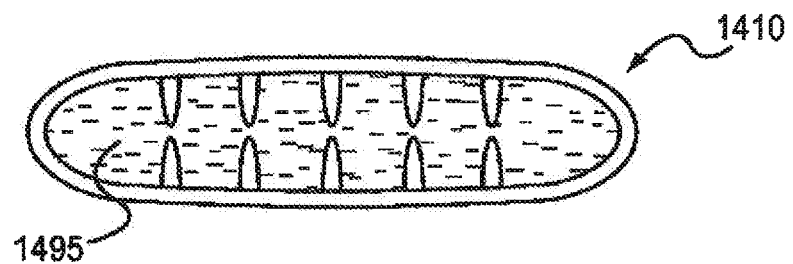
Figures 15, 16A:
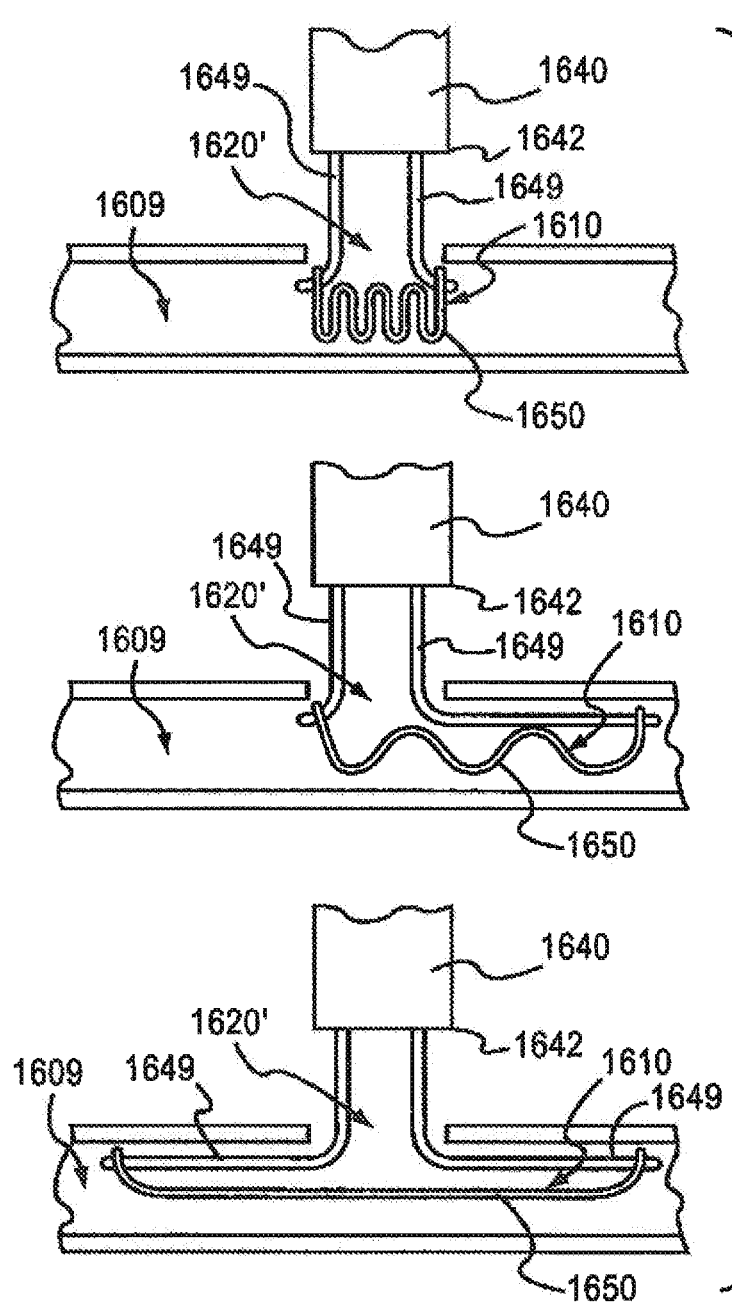
FIG. 16A are side views of a Ward's triangle bore, an actuation device, a pair of actuators, and a support structure according to one embodiment of a device constructed in accordance with aspects of the present invention.

Referring to FIGS. 4-15, various embodiments of femoral neck support structures 110 comprising various stent 112 configurations are shown and described. It should be understood that the support structures described herein are not meant to be limited to the various configurations shown in FIGS. 4-15 or any other figure. FIGS. 4 & 15 comprise example embodiments of a truss or a strut support structure 410 and 1510. FIG. 5 comprises one embodiment of a mesh support structure 510 and FIGS. 6A, 6B and 7 comprise embodiments of a tubular support structure 610 and 710, while FIGS. 8, 10, and 11 comprise embodiments of biasing device support structures such as spring support structures 810, 1010 and 1110. FIGS. 9 and 12 comprise embodiments of coiled or spring structures 910 and 1210, While FIGS. 13 & 14 show expanded support structures 1310 and 1410 adapted to receive filler material 1395 and 1495 (e.g. bone cement), each of the structures in FIGS. 4-15 may comprise expandable support structures adapted to receive filler material 1395 and 1495. Furthermore, it is to be appreciated that each of the structures in FIGS. 4-15 may, in some embodiments, be similar to the structure described in FIGS. 1A-1B.

The stents 112 described herein may be comprised of 316L stainless steel or nickel titanium alloy. However, other material known in the art may also be used. For example, it is contemplated that a polymeric material may be used for the stents 112 and/or the balloons 114 in some embodiments.

Figure 6A:
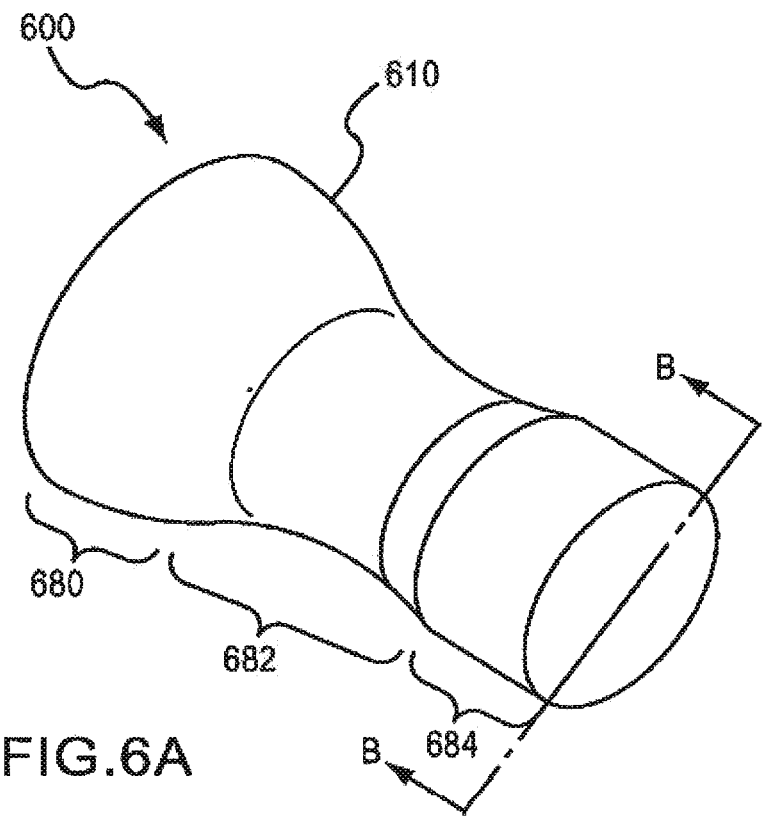
Figure 6B:
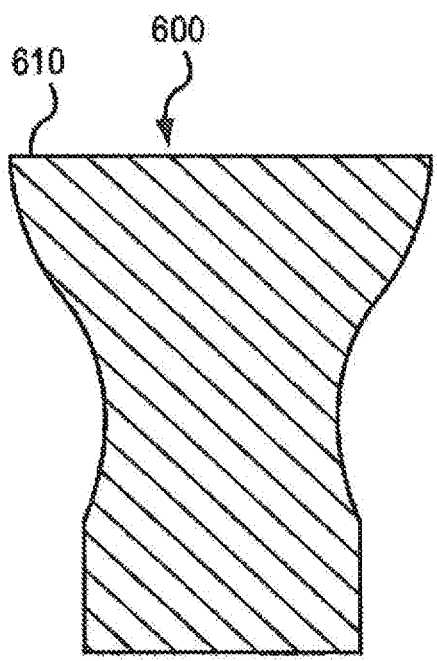
Figure 7:
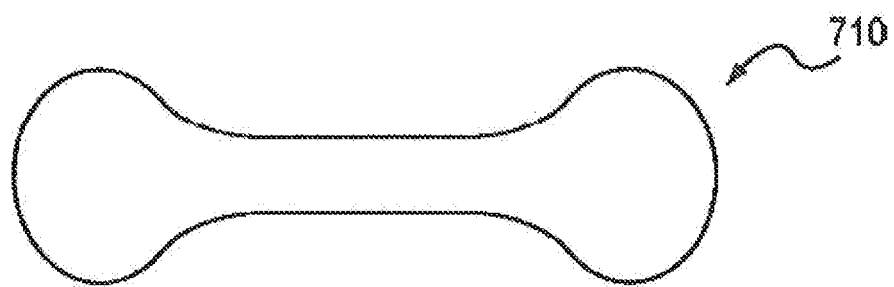
Figure 8:
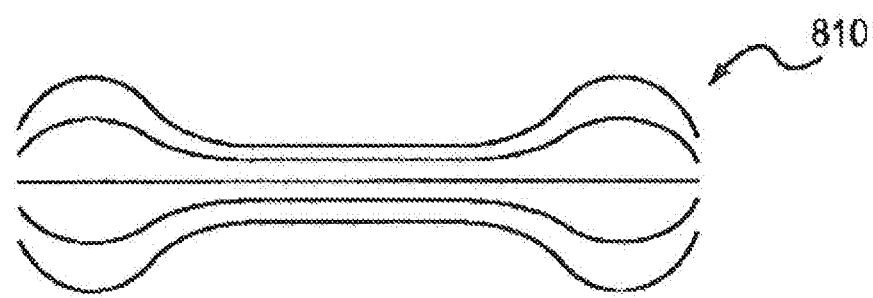

As shown in FIGS. 6A & 6B, one embodiment may be comprised of one or more unitary devices 600. Unitary device 600 may be comprised of an integrated head portion 680, distal neck portion 682, and proximal neck portion 684. Unitary device 600 may further be compressible. For example, unitary device 600 may be a substantially hollow device having a generally hourglass shape comprised of a substantially elastomeric or malleable material. Upon expansion, the unitary device 600 may be adapted to be subsequently filled with filler material.

Figure 16B:
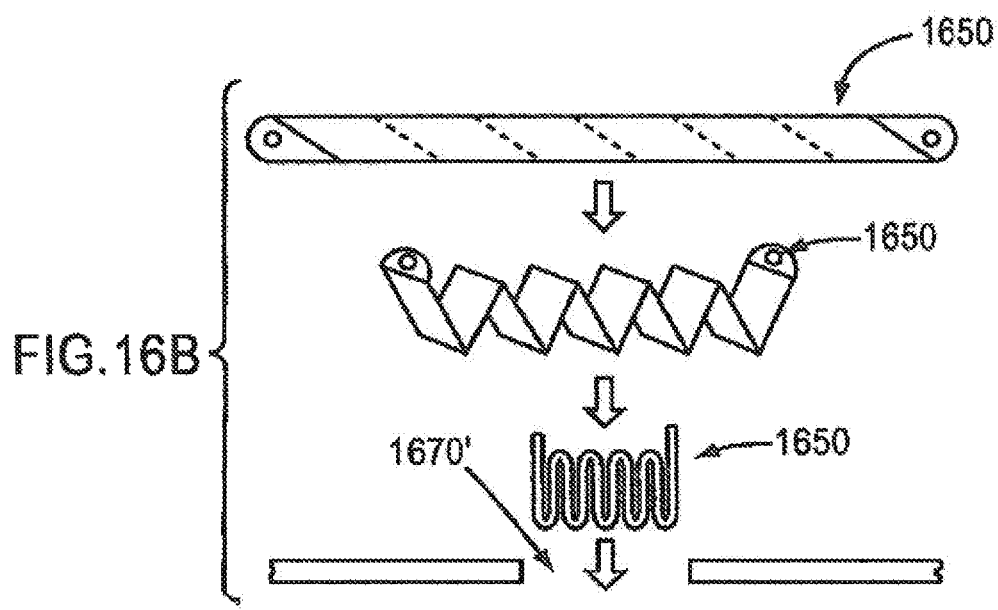
FIG. 16B shows a plurality of views of an accordion-styled support structure according to one embodiment of a device constructed in accordance with aspects of the present invention.
Figure 16C:
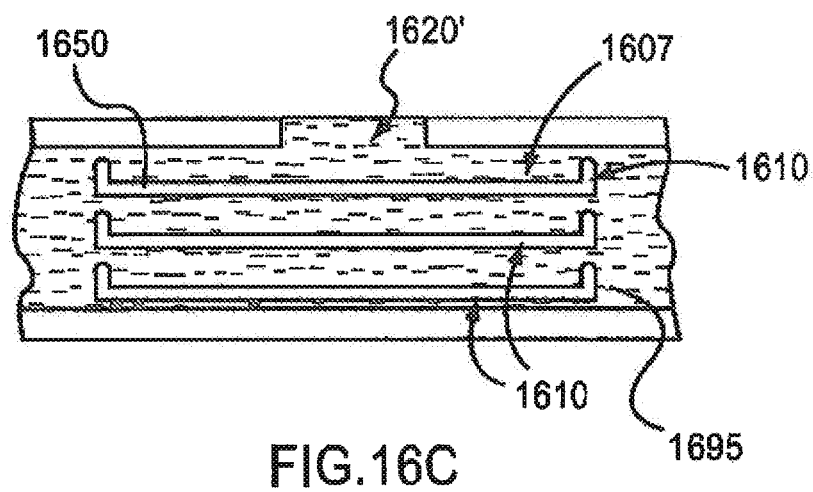
FIG. 16C is a side view of a Ward's triangle bore and cavity having three support structures and filler material located therein.

Looking now at FIGS. 16A-16C, shown is the insertion of one or more compressed accordion devices 1650 into the Ward's triangle bore 1620' and subsequent expansion of the device 1650 in the cavity 1609. One accordion device 1650 may expand upon being inserted through the Ward's triangle bore 1620' upon the use of a pair of actuators 1649 as shown in FIG. 16A. Each actuator 1649 may be adapted to remove the accordion device 1650 away from the actuation device head 1642, placing the device into the cavity 1609. Once in the cavity 1609, a first actuator 1649' may drive one end of the device 1650 in a first direction and a second actuator 1649" may drive an opposing end of the device 1650 in a second direction. The second direction may generally oppose the first direction. These motions may happen sequentially or concurrently. However, embodiments are contemplated which are adapted to use more or less than two actuators 1649 or expand in more than two directions. Furthermore, as shown in FIG. 16C, more than one structure 1610 may be placed within the cavity 1609. Filler material may also be used in the cavity 1609, and in one embodiment, the filler material 1695 may hold the one or more structures 1610 in the proper position within the cavity 1609. As shown in FIGS. 16A-16C, it is also contemplated that one embodiment may interact with bone cement or other filler material 2095 instead of the cortical bone 107 or cancellous bone 108 shown in FIG. 1A.

Figure 17A:
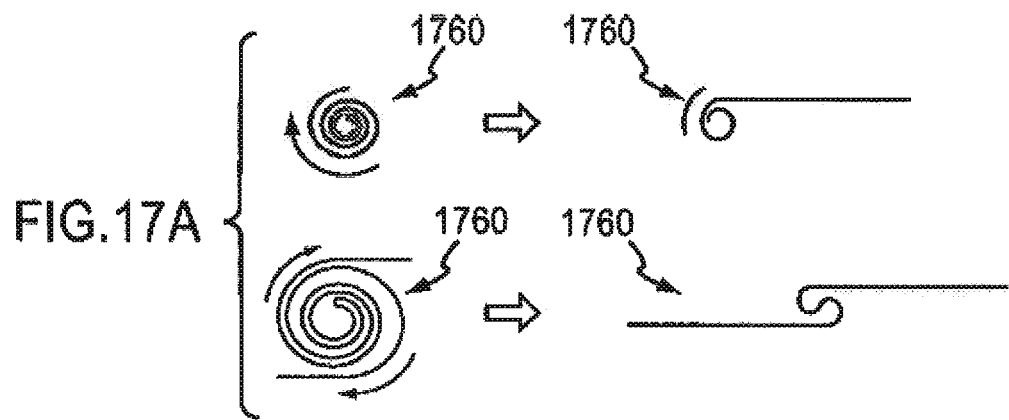
FIG. 17A is a side view of a pair of rotationally deployable support structure sections according to one embodiment of a device constructed in accordance with aspects of the present invention.
Figure 17B:
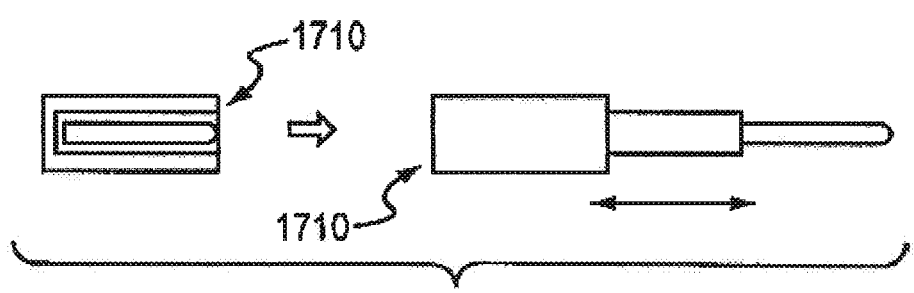
FIG. 17B is a side view of a telescopically deployable support structure according to one embodiment of a device constructed in accordance with aspects of the present invention.
Figure 18:
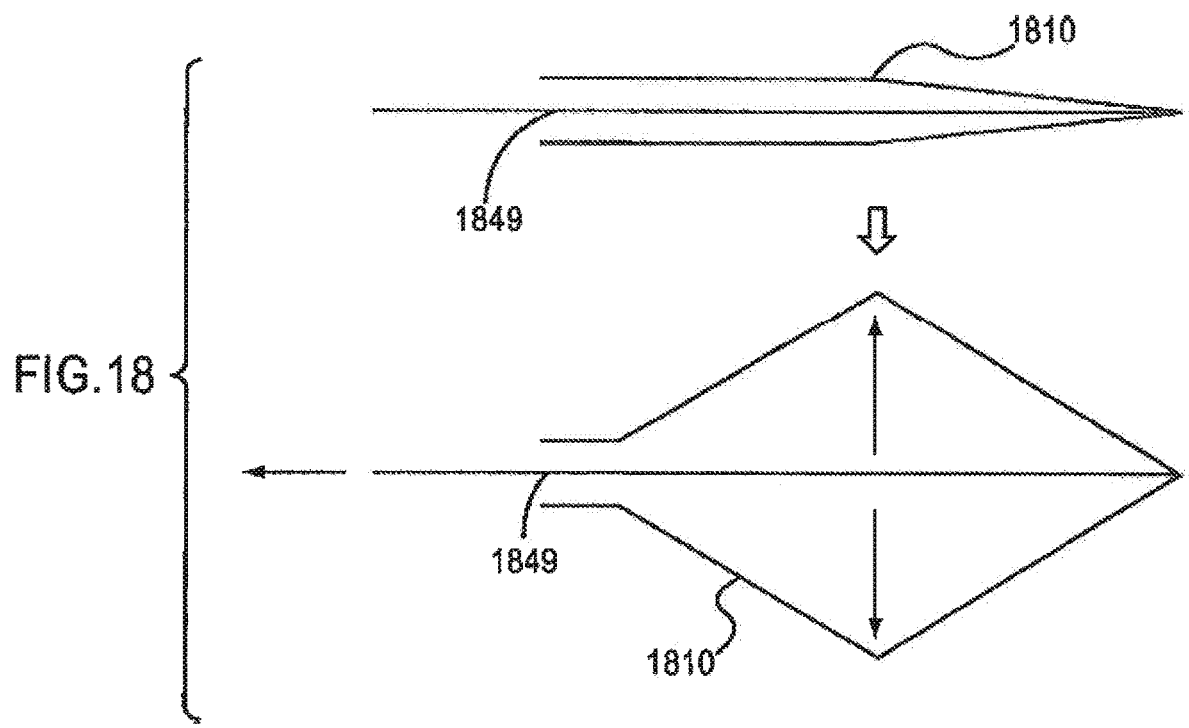
FIG. 18 are side views of a femoral neck support structure adapted to be deployed from a greater trochanter bore according to one embodiment of a device constructed in accordance with aspects of the present invention.

With reference to FIG. 17A, additional devices adapted to expand with or without the actuators 1649 may comprise telescoping support structures 1710, as shown in FIG. 17B, and rotationally deployable devices 1760, as shown in FIG. 17A. The telescoping and rotational devices 1710 and 1760 may be adapted to deploy in a single direction or bi-directionally from either the greater trochanter bore 120" or the Ward's triangle bore 120'. An additional embodiment adapted to expand bi-directionally from a greater trochanter bore 120" insertion location is shown in FIG. 18. As shown, upon applying a single pulling motion to an actuator 1849, the structure 1810 expands bi-directionally. Other devices are also contemplated.

Figures 19A, 19B:
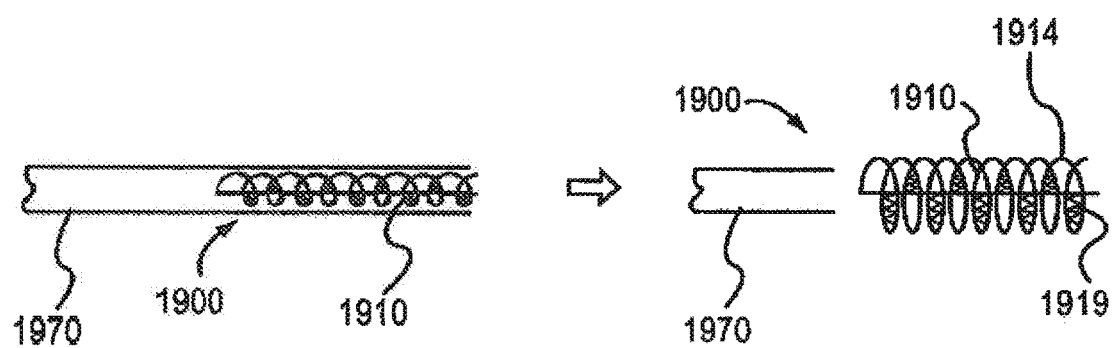
FIGS. 19A-19B are side views of a device comprising a sheath and a support structure according to one embodiment of a device constructed in accordance with aspects of the present invention.

Focusing now on FIGS. 19A-19B in which are shown a device 1900 including a sheath 1970 and a support structure 1910. As shown in FIG. 19A, the sheath 1970 in one embodiment is adapted to substantially surround a compressed support structure 1910. As shown in FIG. 19B, the sheath 1970 is adapted to subsequently be removed to expose the support structure 1910. Upon removing the sheath 1970, for example, by sliding the sheath 1970 in a direction substantially parallel to a structure longitudinal axis (such as, but not limited to, the longitudinal axis 417 shown in FIG. 4), support structure 1910 is adapted to expand. Support structure 1910 may be adapted to laterally expand bi-directionally upon removal of the sheath 1970, although the structure may also be adapted to expand uni-directionally or in more than one or two directions.

For example, as shown in FIG. 19B, the support structure 1910 may be comprised of a biasing device such as, but not limited to, one or more compression springs 1919 which, when the sheath 1970 is removed, expand a stent 1914. Other designs of compressed or coiled support structures 1910 may also be used with the sheath 1970. Furthermore, it is contemplated that an accordion device 1650 may be used with the sheath 1970. In one embodiment, the sheath 1970 may be a portion of the actuation device 340, shown and described in FIGS. 3A-3C.

FIG. 20h comprises a structure 2010 similar in many respects to the structure 210 shown in FIG. 2B. It is to be appreciated that an embodiment of a support structure 2010 is contemplated to have various material properties such as, but not limited to, viseoelastic properties. Furthermore, one embodiment may comprise a structure 2010 having a time dependent or a temperature dependent property. For example, a stent or a filler material 2095 used within a cavity (similar to the cavity 209 shown in FIG. 2B) may become rigid after a certain period of time, or may harden within the cavity upon reaching a certain temperature or upon the application of a certain wavelength of light. Filler material 2095 is also contemplated to comprise a gelatinous material in one embodiment or may comprise a bone growth chemical regulator such as, but not limited to, hyaluronic acid and glycosaminoglycan. Bone growth chemical regulators may be growth factors adapted to locally promote and increase bone density and/or ingrowth into the structure 2010. Many growth factors may stimulate an overall positive level of bone formation in vivo, such as IGF-I, IGF BP-3 and the TGF-Beta family, among others. Other methods and embodiments adapted to increase bone density are contemplated such as including osteoblast cells from an allograft or autograft. Locally promoting bone growth may lead to higher bone density than can be obtained through the use of systemic pharmaceuticals. Filler material 2095 may also be comprised of material such as, but not limited to, cement, glue, adhesive, and foam, or a combination of one or more of these or other materials. Together, the support structure and the filler material are adapted to support and strengthen the femoral neck 2002.

Figure 20:
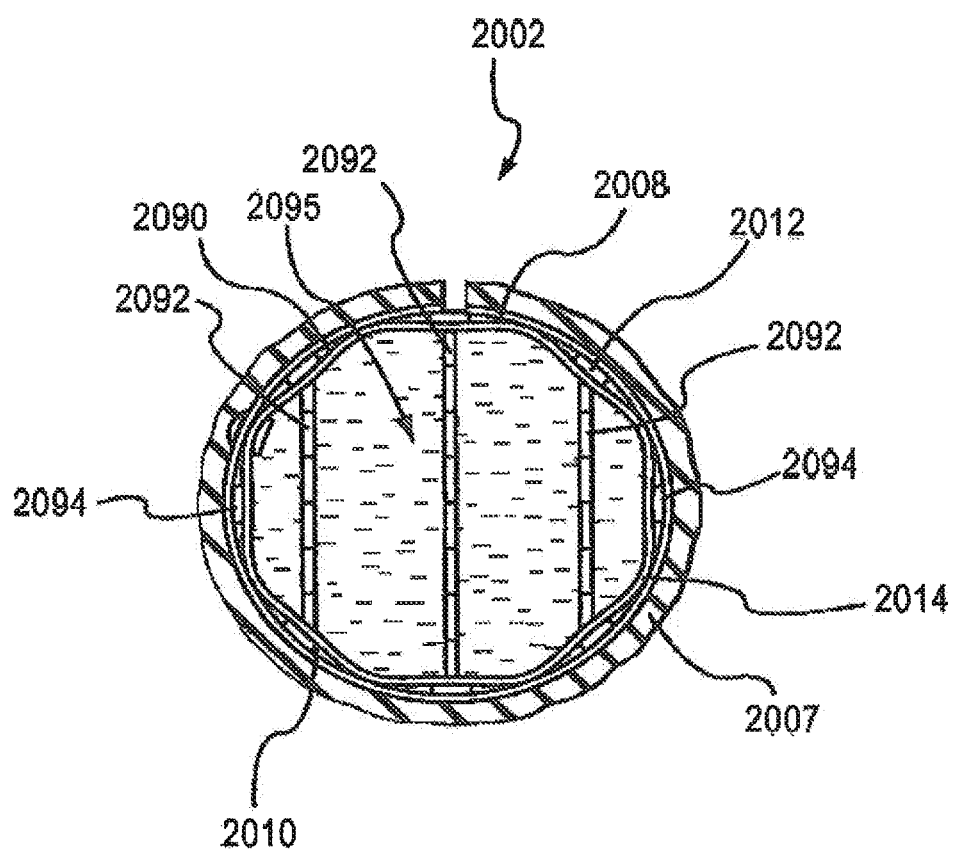
FIG. 20 is a cross sectional view of another embodiment of a femoral neck support structure.

Shown in FIG. 20 is a femoral neck support system 2090. A femoral neck support system may be comprised of the support structure 2010. The support structure 2010 used within the support system 2090 is similar to the support structures described elsewhere herein. For example, the support structure 2010 may be comprised of at least one balloon 2014 or may be comprised of at least one spring, similar to the plurality of springs shown in FIG. 19B. Like the previously described support structures 2010, the femoral neck support system 2090 defines at least one internal cavity. For example, as shown in FIG. 2B, the expanded balloon 214 defines an internal space comprising the cavity 209. Furthermore, the support structure 2010 may be comprised of internal support beams 2092 and external support beams 2094. The internal support beams 2092 may extend through the cavity while the external support beams 2094 may extend along a cavity edge. Although shown as being perpendicularly aligned in FIG. 20, it is contemplated that some internal and external support beams are not perpendicularly aligned. The filler material 2095 is adapted to fill the space between opposing external support beams 2094 and around the internal support beams 2092.

Figure 3D:
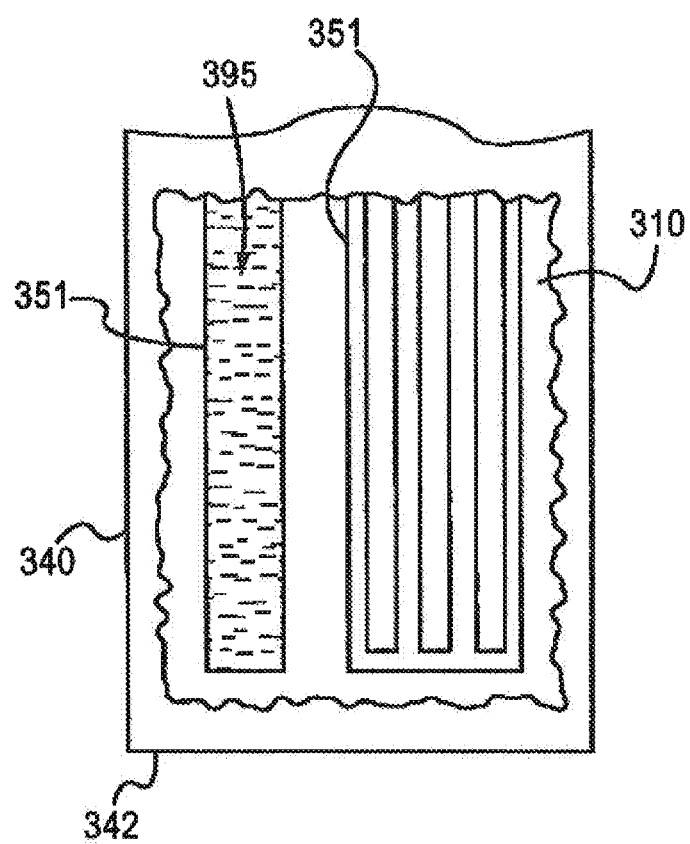
FIG. 3D is a side view of an actuation device head cut-away portion showing two lumens.

The actuation device 340 shown in FIGS. 3A-3B may also be adapted to deliver filler material 395 to an internal cavity. For example, as shown in FIG. 3D the actuation device 340 may comprise at least one lumen 351 adapted to deliver the filler material 395 to the cavity and at least one other lumen 351 adapted to deliver the structure 310. Lumens 351 having other support system components such as, but not limited to, the sheath 1970 shown in FIGS. 19A & 19B, are also contemplated.

In viewing FIGS. 1A, 4, and 20, embodiments of a support structure 110, 410, and 2010 having filler material 2095 may be oriented along a longitudinal axis 417 while being subjected to a maximum peak gait load 135 or a lateral fall load 130. One lateral fall load 130 may also be referred to as a first load and a one peak gait load 135 may also be referred to as a second load. In one embodiment, the filler material 2095 and structure 410 may be adapted to receive a maximum peak gait load 135 of about 7 kN before plastic deformation or structural failure occurs. One peak gait load 135 may be applied generally parallel to the longitudinal axis 417. However, it is understood that the loads 130 and 135 discussed herein and applied to the femoral neck 102, support structure 410, 110, and 2010, and filler material 2095 may vary over time, direction, and location. Therefore the loads 130 and 135 in FIG. 1A are only generally representative of peak gait and lateral fall loads on the device 100. For example, one peak gait load 135 may be applied thirteen degrees off a vertical plane and may be centered at a different location on the femoral head 105 than what is shown in FIG. 1A. Likewise, it is to be appreciated that the lateral fall load 130 direction may be applied 30 degrees off a horizontal plane and a different location than what is shown in FIG. 1A. In one embodiment, a maximum lateral fall load 130 that one support structure 2010, 410, 110 and filler material 2095 may be adapted to receive without plastic deformation or structural failure is about 12 kN. The lateral fall load 130 may also be applied generally perpendicular to the longitudinal axis 417 of the support structure 410.

Figure 21A:
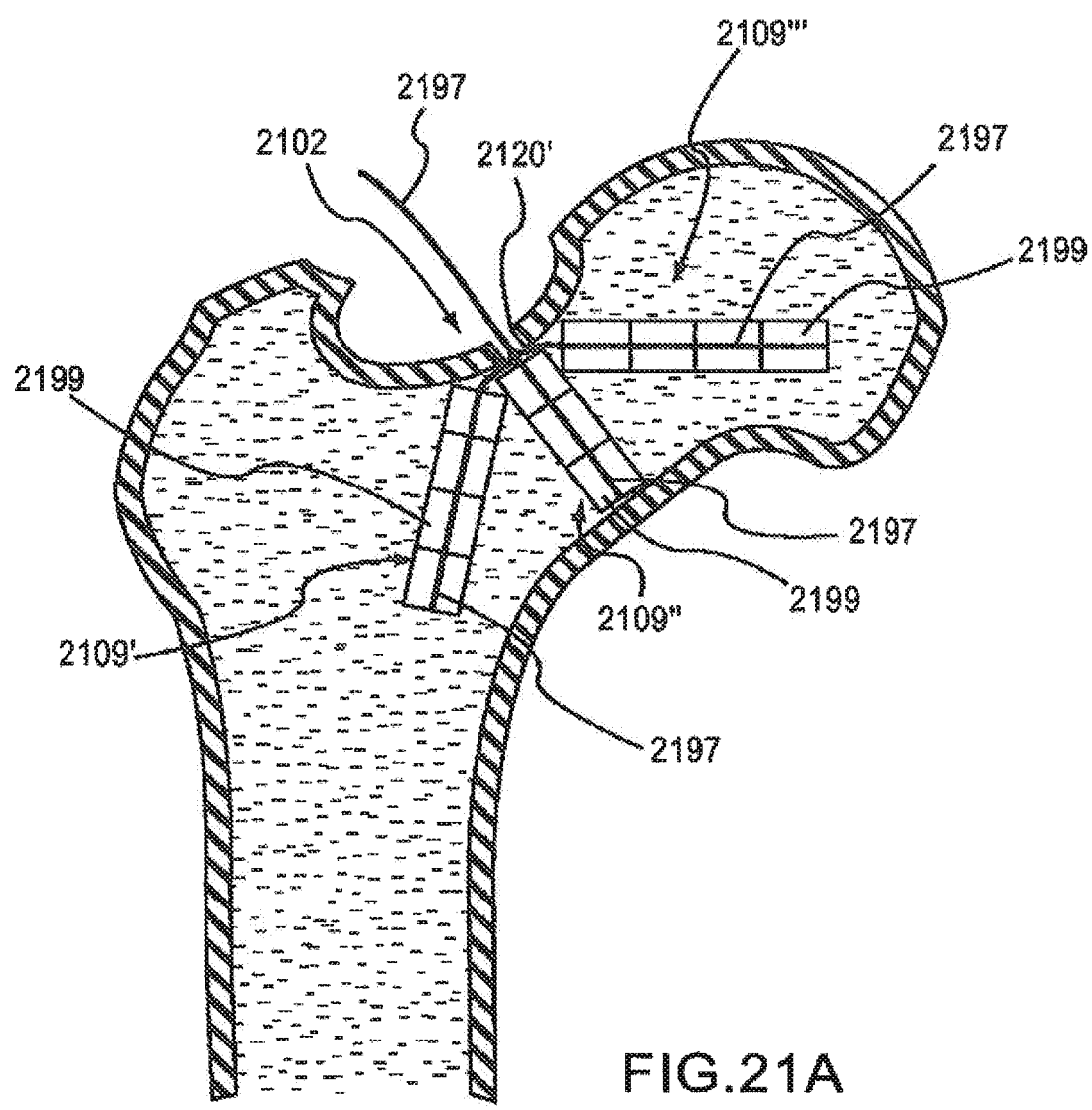
FIG. 21A is a side-view of another embodiment of a femoral neck support structure and a cross-section of a femoral head, neck and body portions.
Figure 21B:
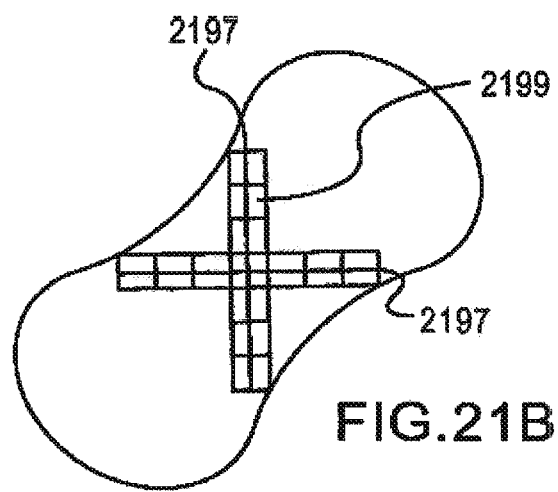
FIG. 21B is a top view of a femoral neck support structure placement within a femoral head.

As shown in FIGS. 21A-21B, one further embodiment may be comprised of at least one guide wire 2197 and a plurality of support blocks 2199. The support blocks 2199 and guide wires 2197 may be delivered to the femoral neck 2102 through the actuation device 340 described in FIGS. 3A-3D. In one embodiment, the guide wires 2197 may be inserted into one or more cavities created within the femoral neck 2102. For example, a balloon or other device may create a first cavity 2109', a second cavity 2109" and a third cavity 2109'''. Upon insertion of the guide wires 2197 to the cavities 2109', 2109'', and 2109''', the support blocks 2199 may be delivered along the guide wires 2199 into the cavities. Each support block 2199 may be adapted to couple to each adjacent support block 2199. Upon correctly positioning the support blocks 2199, filler material 2095, as shown in FIG. 20, may be introduced into, and the guide wires may be removed from, the cavities. In one embodiment, once positioned, the support blocks 2199 may generally comprise a cruciform shape, as shown in FIG. 21B.

Figure 2A:
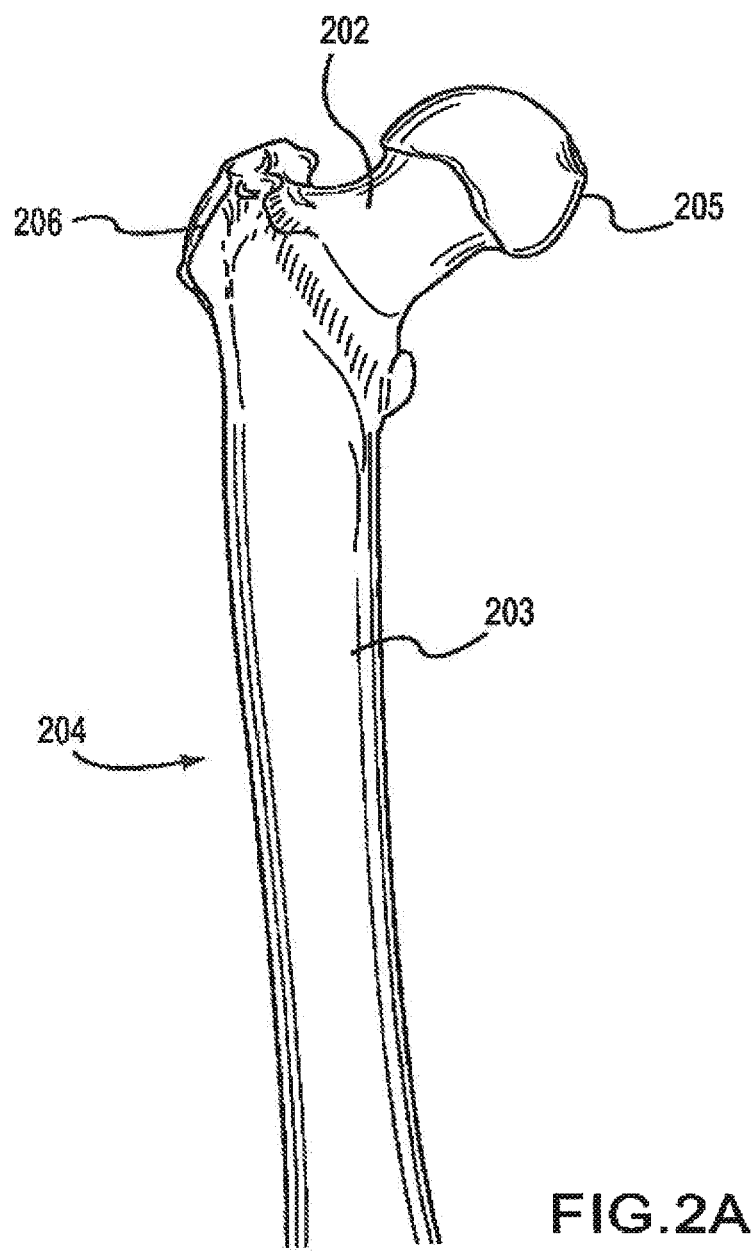
FIG. 2A is a side view of one example of a femoral body, neck, and head.
Figure 2B:
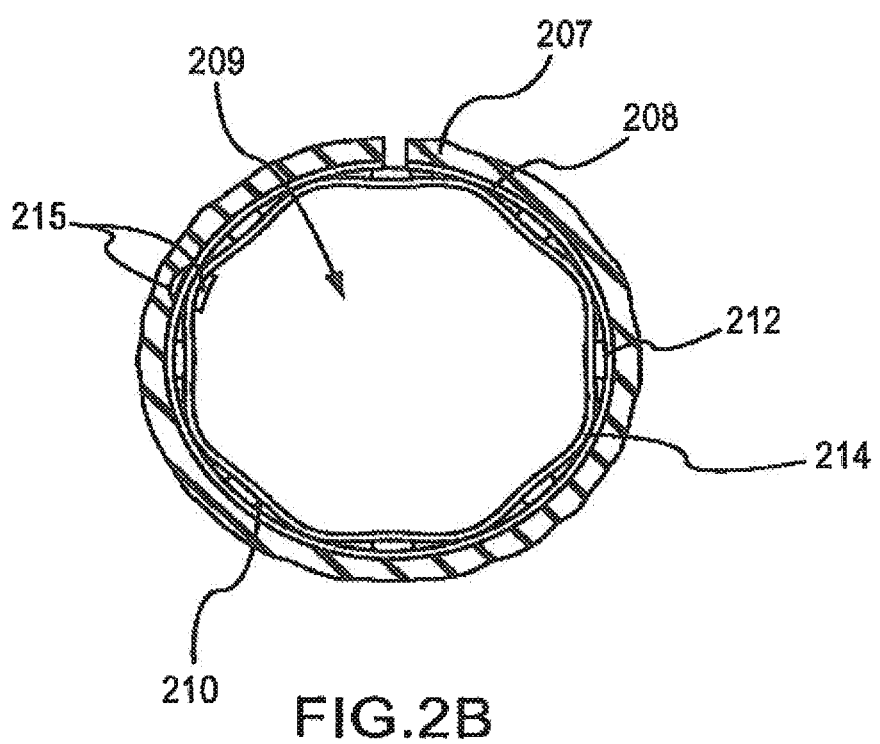
FIG. 2B is a cross-sectional view of the femoral neck having an expanded support structure placed therein along line A-A of FIG. 1A.
Figure 22:
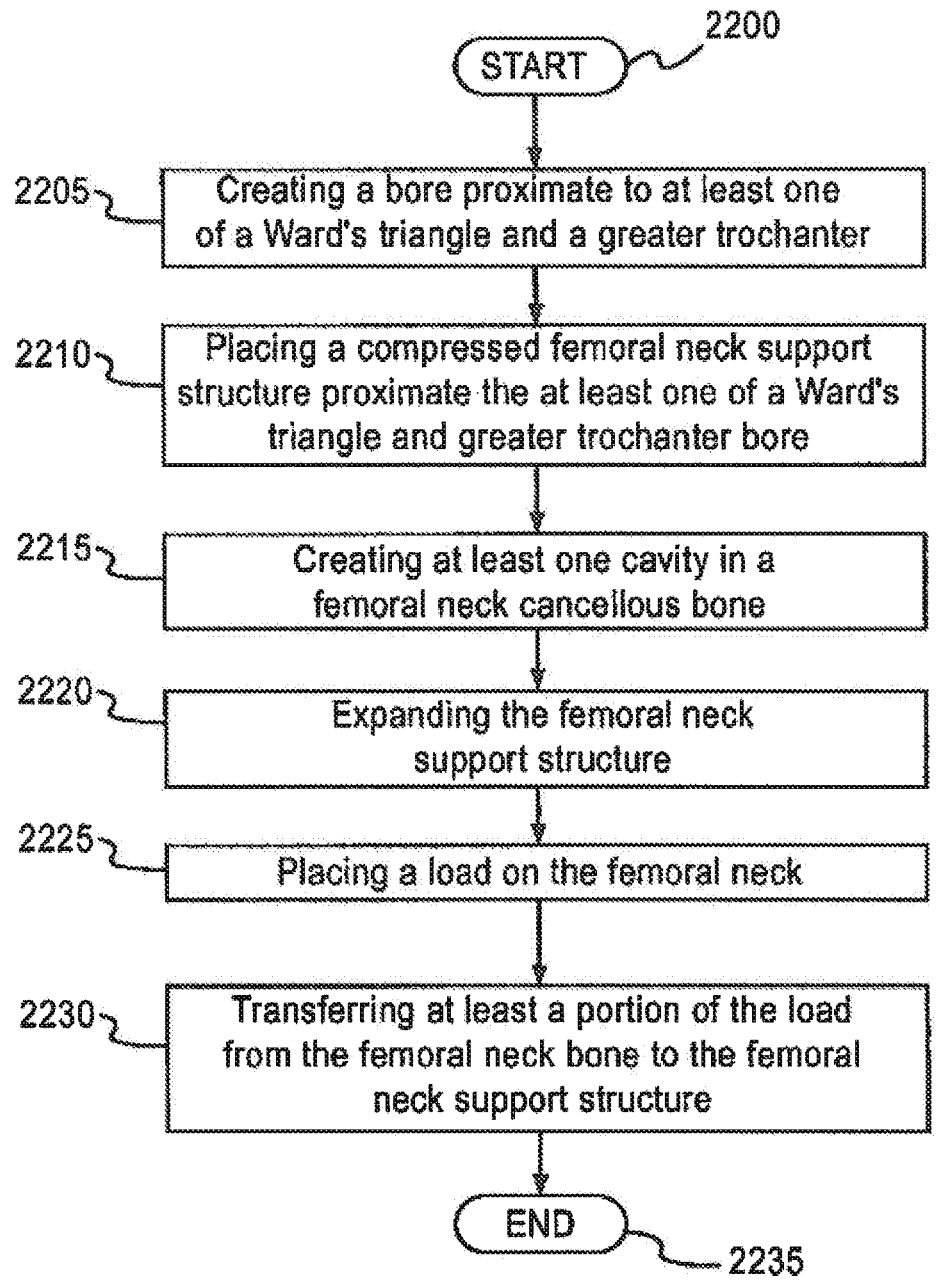
FIG. 22 is one embodiment of a method of reinforcing a femoral neck.

In now looking at FIG. 22, with reference to FIGS. 1A & 2A, shown is a method of reinforcing a femoral neck 102. The method starts at 2200. At 2205, a bore is created proximate to at least one of a Ward's triangle and a greater trochanter 206. The at least one bore may be created with a drill such as, but not limited to, a coring drill, or other device such as, but not limited to, a chisel or pick, and used to access the cancellous bone 108 within the femoral neck 202. At 2210 a compressed femoral neck support structure 110 (as shown in FIG. 1B) is placed proximate the at least one of a Ward's triangle bore 120' and greater trochanter bore 120''. Correct placement of the device may occur through the use of an actuation device 340, as shown in FIG. 3A. Specifically, a steerable actuation device 340 may be used. At 2215, at least one cavity is created in a femoral neck cancellous bone 108. However, the at least one cavity may also be created in a greater trochanter 206 and/or a femoral head 208 cancellous bone area. The at least one cavity may be created by expanding a balloon 114 and compressing a portion of the femoral neck cancellous bone 108. The balloon 114 may also be placed in the correct position by the actuation device 340. At 2220, the femoral neck support structure 110 may be expanded. Expansion in one method may occur through expansion of the balloon 114. In order to reinforce the femoral neck 102, when a load is placed on the femoral neck, as shown at 2225, at least a portion of the load is subsequently transferred from the femoral neck bone to the femoral neck support structure 110, as shown at 2230.

Additional methods may include variations of the described steps above and may include further steps such as coupling the support structure to healthy bone material. For example, the support structure may be coupled to healthy cortical bone or structurally active compressed cancellous bone using bone cement, clips, or staples. Other methods of coupling the support structure to healthy cortical bone may include through friction between the device and the bone or compression force between the device and bone. Filler material may be introduced into the cavity. At least a portion of the load applied to the femoral neck may then be transferred the support structure and the filler component. Finally, it is contemplated that a fluid may be introduced into the cavity. However, a fluid introduced to the cavity would likely be contained and enclosed by a fluid containment structure such as, but not limited to, a balloon.

Figure 23:
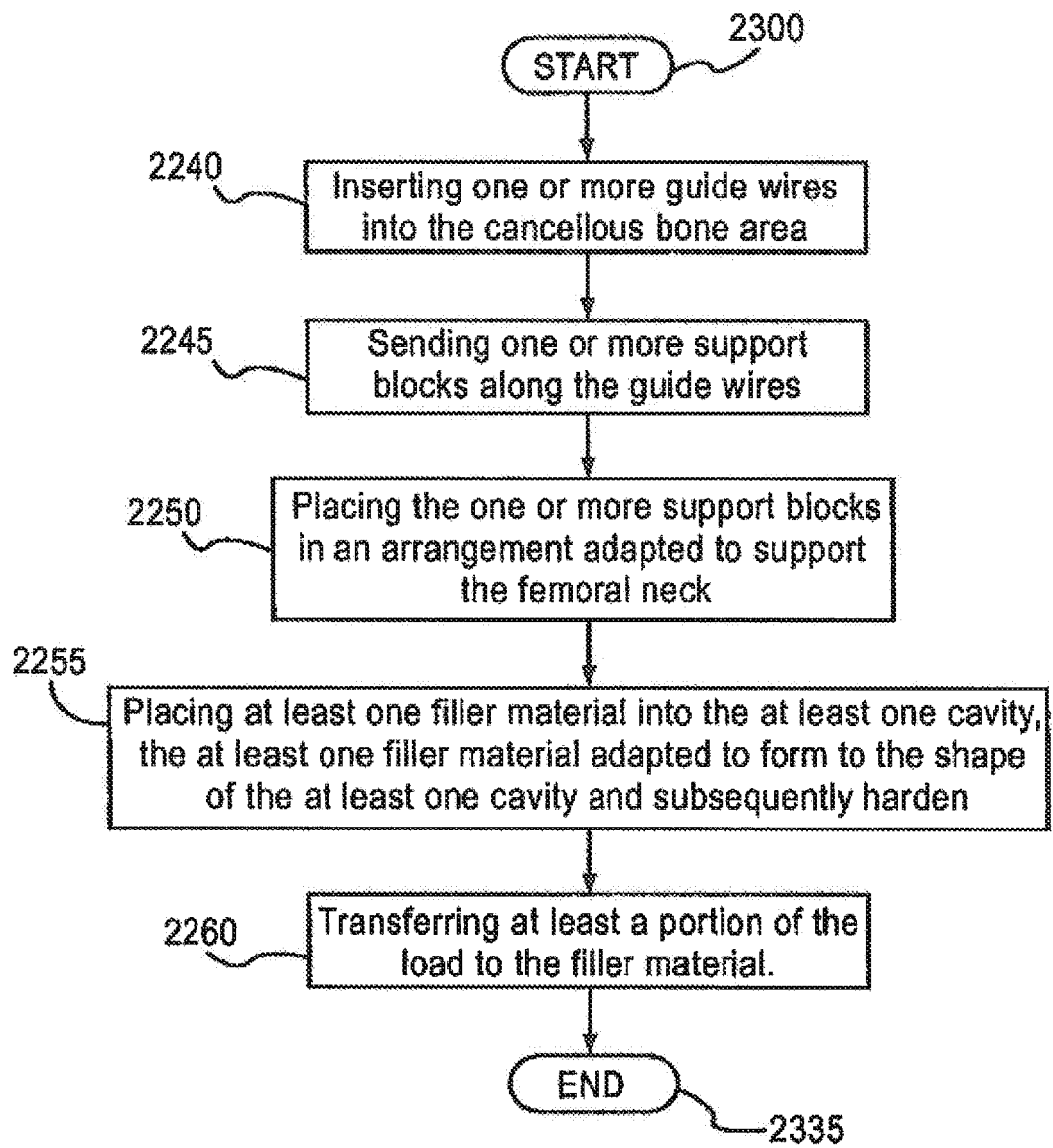
FIG. 23 is another embodiment of a method of reinforcing a femoral neck.

Some of these steps, and others, are shown in FIG. 23. In one embodiment, the start of the method of FIG. 23, at 2300, begins at the end of the method of FIG. 22. The additional steps include, at 2240, inserting one or more guide wires into the cancellous bone area. This may involve inserting a polymeric or 316L stainless steel wire into a cavity created in the cancellous bone of the femoral neck. Once the wires are in position, the method continues at 2245, where one or more support blocks are sent along the wire into the cancellous bone area. Upon reaching the correct position, the one or more support blocks may be positioned in a position adapted to support the femoral neck at 2250. Although one support position may be a generally cruciform position, as shown in FIG. 21B, other support block positions are also contemplated. Filler material is placed into at least one cavity at 2255, the filler material adapting to form to the shape of the at least one cavity and subsequently harden. Finally, at 2260, a portion of the load is transferred to the filler material, in addition to a portion of the load being transferred to the support structure at 2230.

Figure 24:
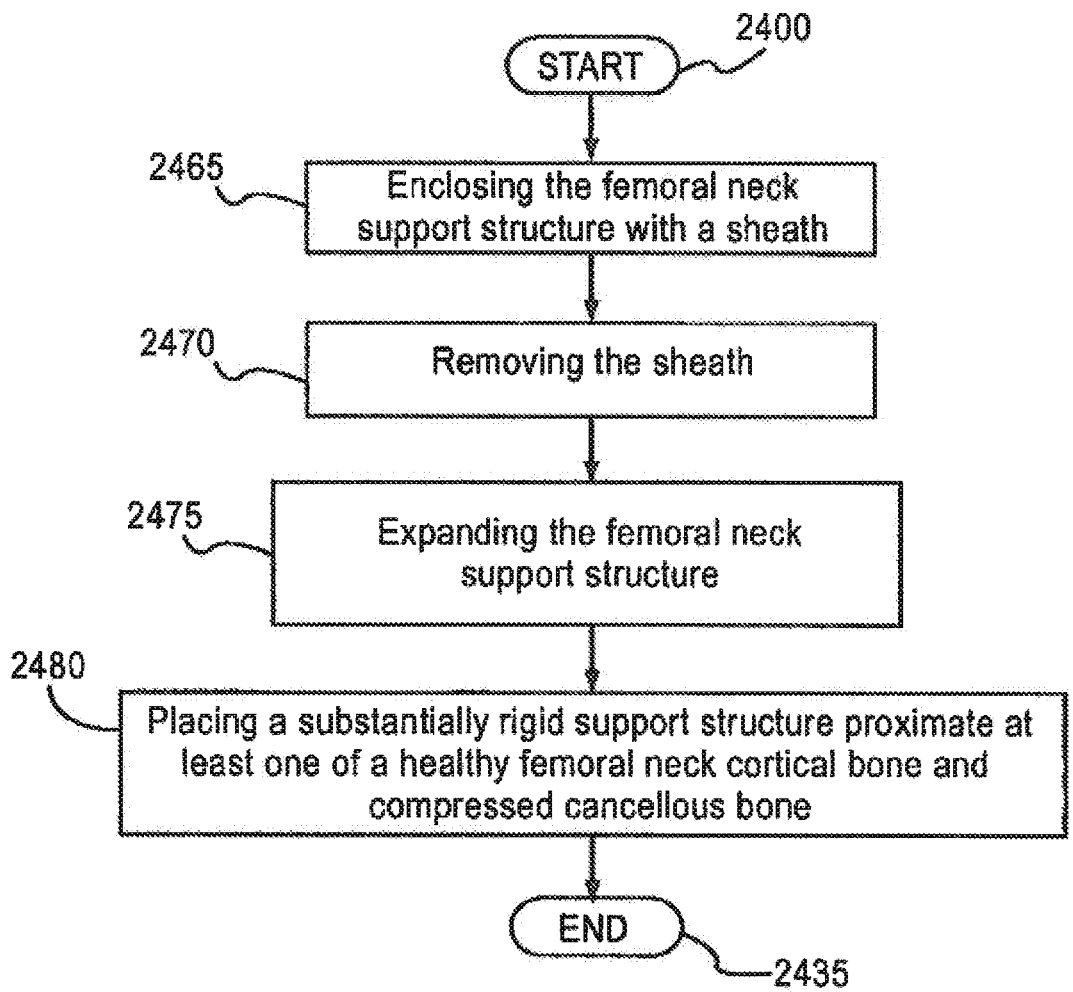
FIG. 24 is yet another embodiment of a method of reinforcing a femoral neck.

Referring to FIG. 24, shown is another method for reinforcing a femoral neck where in one embodiment the start of the method of FIG. 24, at 2400, begins at the end of the method of FIG. 22. At 2465 the femoral neck support structure is enclosed with a sheath. This may comprise enclosing a compressed support structure such as, but not limited to, the compressed support structure shown in FIG. 1B. At 2470 the sheath is removed and at 2475, the femoral neck support structure is expanded. For example, the sheath may be adapted to keep the support structure in a compressed position and upon removal the support structure may be adapted to expand. Finally, at 2480, a substantially rigid support structure is placed proximate at least one of a healthy femoral neck cortical bone, a compressed cancellous bone, or bone cement placed within the femoral neck. In one embodiment, the substantially rigid support structure is created upon removal of the sheath and expansion of the structure. In another embodiment, expansion of a support structure may also occur through one of twisting, pulling, and pushing an actuation device.

Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention.

The invention claimed is:

1. A device for reinforcing a femoral neck bone, the femoral neck bone including a cortical bone region and a cancellous bone region, the device comprising a support structure having an outer surface, and including a portion comprising one or more bores through which an expandable portion of the support structure is capable of being released into the cancellous bone region, the one or more bores further adapted to allow filler material to be released therefrom to enter directly into the cancellous bone or into the cancellous bone along with the expandable portion of the support structure, wherein further the expandable portion of the support structure is formed at least partially from a material that increases its rigidity after a period of time after being released.

2. The device of claim 1, wherein the filler material is bone cement.

3. The device of claim 1, wherein the filler material comprises a gelatinous material.

4. The device of claim 1, wherein the filler material comprises a material selected from one of the group consisting of glue, adhesive, and foam.

5. The device of claim 1, wherein the filler material comprises a bone growth chemical regulator, wherein the bone growth chemical regulator is preferably selected from one of the group of hyaluronic acid and glycosaminoglycan.

6. The device of claim 1, wherein further the support structure section physically couples with at least a portion of the internal cancellous bone region when the support structure section is released into the portion of the cancellous bone region.

7. The device of claim 1, wherein the support structure section is formed at least partially from a material that increases its rigidity upon the application of a certain wavelength of light.

8. The device of claim 1, wherein the support structure section is formed at least partially from a material that increases its rigidity upon the application of a certain temperature, preferably body temperature.

\* \* \* \* \*